United States Patent
Ueyama et al.

(10) Patent No.: US 6,225,453 B1
(45) Date of Patent: May 1, 2001

(54) **PROBES FOR THE DIAGNOSIS OF INFECTIONS CAUSED BY *KLEBSIELLA PNEUMONIAE***

(75) Inventors: Hiroshi Ueyama, Osaka; Kanako Abe, Yawata; Hiroyuki Keshi; Akio Matsuhisa, both of Osaka, all of (JP)

(73) Assignee: FUSO Pharmaceutical Industries, Ltd., Osaka (JP)

( * ) Notice: Subject to any disclaimer, the term of this patent is extended or adjusted under 35 U.S.C. 154(b) by 0 days.

(21) Appl. No.: 09/402,002

(22) PCT Filed: Mar. 23, 1998

(86) PCT No.: PCT/JP98/01286

§ 371 Date: Jan. 10, 2000

§ 102(e) Date: Jan. 10, 2000

(87) PCT Pub. No.: WO98/42843

PCT Pub. Date: Oct. 1, 1998

(30) Foreign Application Priority Data

Mar. 25, 1997 (JP) .................................................. 9-071082

(51) Int. Cl.[7] .............................. C07H 21/04; C12Q 1/68
(52) U.S. Cl. ................... 536/23.1; 536/24.32; 536/24.3; 536/24.33; 435/252.1; 435/6
(58) Field of Search ................................ 536/23.1, 24.32, 536/24.31, 24.33, 24.3; 435/252.1

(56) References Cited

U.S. PATENT DOCUMENTS

| | | | | |
|---|---|---|---|---|
| 5,192,675 | * | 3/1993 | Chatterjee et al. | 435/199 |
| 5,487,987 | * | 1/1996 | Frost et al. | 435/142 |

OTHER PUBLICATIONS

Nijkamp, H.J. et al., "The Complete Nucleotide Sequence of the Bacteriocinogenic Plasmid CloDF13," *Plasmid*, 16(2):135–160 (Sep., 1986).

PCT International Preliminary Examination Report, International Application No. PCT/JP98/01286 filed Mar. 23, 1998, dated Feb. 14, 2000.

* cited by examiner

*Primary Examiner*—W. Gary Jones
*Assistant Examiner*—Jeanine Goldberg
(74) *Attorney, Agent, or Firm*—Marshall, O'Toole, Gerstein, Murray & Borun

(57) ABSTRACT

The DNA from the bacteria *Klebsiella pneumoniae* is extracted, then completely digested with restriction enzyme Hind III, followed by cloning into a suitable vector to select a probe comprising DNA which is essentially contained in *Klebsiella pneumoniae*, then the sequence of the probe is elucidated.

9 Claims, 1 Drawing Sheet

FIG. 1A
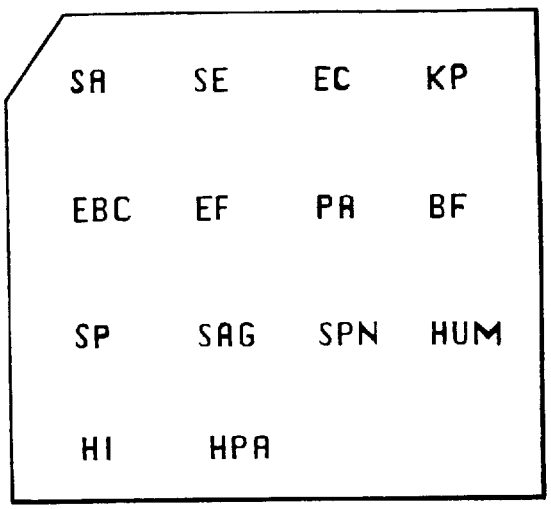
SA:*S.aureus* /SE:*S.epidermidis* /EC:*E.coli* /KP:*K.pneumoniae* /
EBC:*E.cloacae* /EF:*E.faecalis* /PA:*P.aeruginosa* /BF:*B .fragilis* /
SP:*S.pyogenes* /SAG:*S.agalactiae* /SPN: *S.pneumoniae* / HUM:
U937 genomic DNA /HI:*H.influenzae* /HPA:*H.parainfluenzae*
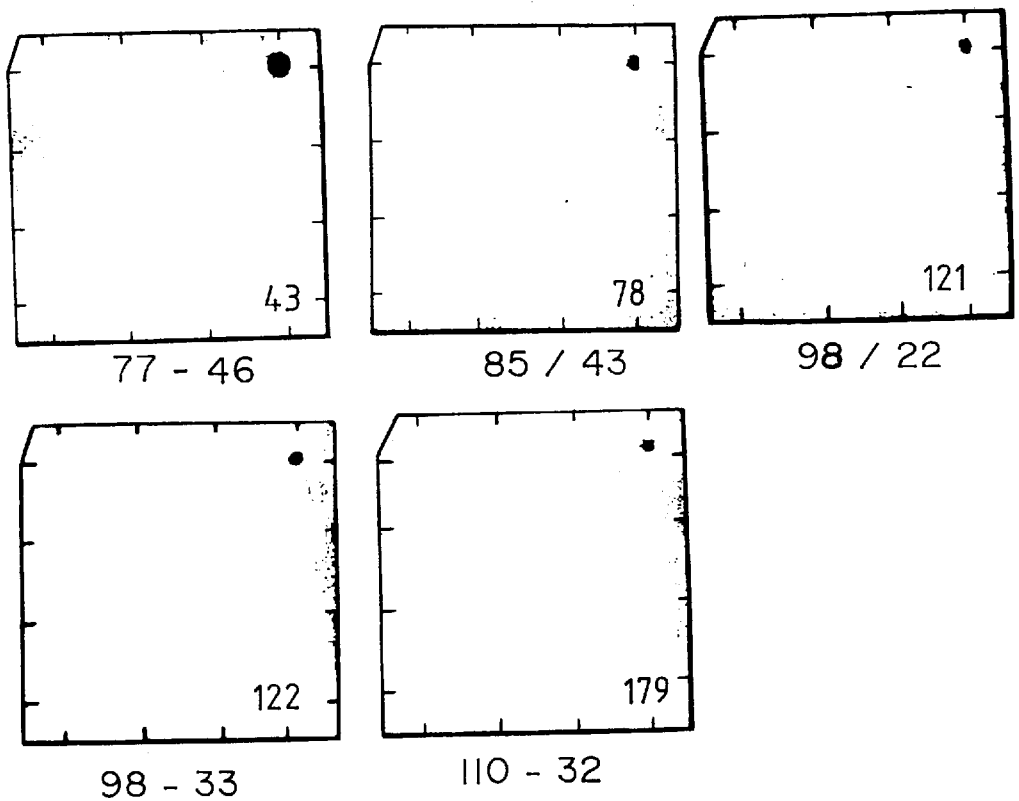
FIG. 1B

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
    (A) LENGTH: 1941 base pairs
    (B) TYPE: nucleic acid
    (C) STRANDEDNESS: double
    (D) TOPOLOGY: linear (ii) MOLECULE TYPE: DNA (genomic)

(vi) ORIGINAL SOURCE:
    (A) ORGANISM: Klebsiella pneumoniae
    (B) STRAIN: Clinical Isolate KP-77-46

(ix) FEATURE:
    (A) NAME/KEY: misc_feature
    (B) LOCATION: 1462
    (D) OTHER INFORMATION: /note= "N = adenine or cytosine or
       guanine or thymine"

(xi) SEQUENCE DESCRIPTION: SEQ ID NO: 1:

```
AAGCTTATCC CGCATCACCT GCCAGAGTGT TTCCGCATCC TCGTGCAGCC GCTCGCACAT      60
GTCGGCCGGG GTATCCATAT CCAGCTCGTT CAGTTTCTCG AGCAACAGCA GCGACTGGTC     120
CTTAATGAAT TTAGCCATAT TGAGGGCGGT TTTTTCCTGC TTCGTCATGT TCTCCATTCC     180
CTTCGGTAAG TTCTCAGCTA AACCAGCCGG ACCAGAAGCG TTTTTTCTTC TGTGTCAGTT     240
CTGTTGTCAA TCTGTCCACT TCGGCCTGGA GTTTCCGGCG CTCATCATCG TGCTGGCGGC     300
GTTCTTCTTC CCGGGATGTT TTATCTTCCA GCATCAGGGT GACAGCCTGC CGGAGATCGG     360
CCAGTTCCTT TTGCATTGCC AGAAGCTGTT CCTGTGGGAA ATTTTTTTGT GTATTTTCAC     420
GGTGTGAAAT GCCGGGAATT TGTTTCTCAG GGATATTCAC ATTTCCGTAT ACACGGATCA     480
GTTCTGACAC ATCCACGACA GGGTTGTTTT TCCCGTCACG TGACACGGTA ACCTTTCCCT     540
GTTTTACATG ATTGTATAGC GTTCTTCTGG TAATGCCCGC GGCTTGTGCT GCCTGTGAAA     600
GGTTGAGCAA TGTTTTCGCC ACTGTATACC CCTGATTTTA TCGGGTGTGA AAGGTGTGTA     660
ATTTCTCACG GTAAATGTAT CGCTGAATTT TACCCGTTTT TCCGTTCAGG ATGTGGTTTT     720
CTGACGCGCT GTGCTTGTCA AACCGGCGAC GGCCACGCAA TGAATTGCGC CCCCGTCATC     780
GGTTATTAGA GGCTGTCTGC CCCCGGATAC CCGGATTCTT TCTGATGCCT GACGGTGACG     840
ATCACAATCC GGTCCATTTC CCGGTCGTGG CGGTAGAGCA TCACATAGCC ACTGTCGCCA     900
AACCCGATCA CCAGTTCCTG ATATTCCAGC GGCAGAAATG GCACCGGGCG GCCAATGTCT     960
GGCAATGTTT TCAGTTGCTG GATAGCCCGG ACGATCACCT CACCGGCTTT TCTGGCTGCC    1020
AGCCGATTTT TGGTTTTGAG AAAGTCCTGG AGGCGTTGTA AATCCTCCTG TGCCAGCGCG    1080
GAAATCGTTA CCTGTGGCAT GGCGGAGCAT CCTGCTCGTT CTCAGTTCCC CAGGTACTTA    1140
TCCAGGCTTC TGCTTCTTCC GCAGTAAGGT GCAGACCCGT TTCCTGATAG TGCTGCCATG    1200
CGGCTTGTCC GTCCCGCAGG TACTGGTGCG CTTCTCTTCC CGGTCGATGT ATTCGGTGAT    1260
TGCCTCCAGC ATTAGCGCGT GCGCTGAGCG GTGCCGGTCA TCGGCCAGCG TTTTCAGCCG    1320
GTCCTTAAGT TCTTCATCGA GCCTGATGGA TGTTGCTGAT GACATAAAAG CCCCTTTGTA    1380
GTCATGTGTA ATACATATGA CTACTTTAAT CCGTGGCGGC GCTATTTGCC AGAAATACGG    1440
CTTTTGCTGC CCATTTTTTC ANTTCGCTTC CCCATTTTTT CACTTCGCTT CCCCATTTTT    1500
```

```
TCACTTCGCT TCCACTAATC AGGGCTGCTA CAGGCTCACT CATCATCCAG GACTATTGCA      1560

GCCTGCGGGT TAAAGGACCT GTTACTGGCG GCAACCATCA TCATTGAACT TTTTGGTGGT      1620

GGCTGGTCGC GGATCCTGTA AGCCGTCATT TTTCAGACTG AATTCAAAAT TTATAACCTG      1680

TCGCATTGCC GGGTGCCTGC GGGATATAGC CAGTGCCTCA TTGCCGTCAG CGTTTCCCGA      1740

AAAAAAAGTG ACAGCCGGTA AGCGACACGT TGTCCACTCG TCCATCGTCC AGAATATCAA      1800

ACGTGGCGGT CACCTGACCT TCGATGCGTT TTGCTGCGGC CTGTACCGGG TAGGTTGGCT      1860

GCAGTGTGGT TACGGGTTTT AGTGGTATCG CATGTACCGG AGTGAGGAAC ATGGCCGCCA      1920

GCACTGTCAG AGTAAAAGCT T                                                1941

(2) INFORMATION FOR SEQ ID NO: 2:

(i) SEQUENCE CHARACTERISTICS:
         (A) LENGTH: 1747 base pairs
         (B) TYPE: nucleic acid
         (C) STRANDEDNESS: double
         (D) TOPOLOGY: linear (ii) MOLECULE TYPE: DNA (genomic)

(vi) ORIGINAL SOURCE:
         (A) ORGANISM: Klebsiella pneumoniae
         (B) STRAIN: Clinical Isolate KP-85-43

(xi) SEQUENCE DESCRIPTION: SEQ ID NO: 2:

AAGCTTTTCT TTCAACCCTG ACAAGATGG CTGAAAAGCA GAAGAACACA GGTAAAGAAA        60

TGTTCGTGGG TGTCAACCGG GTACTGAGCG ATGCAGAATC AAAATCATTT TTCGAAGAAA      120

ACAGAACGCA GTACCCAAAG ATGGACATTA AAATACCGTT TCTTACGGTG CGCGAAACTC      180

TTCTGTACAA ACCCGCATTG AATGCCTCAC AGGTGATGTG CCCGACCCTG ATCGTTATTG      240

CTGGTCAGGA TACGGTTAAT CCACCGGAGC AGGGACGGGC CTTATTTGAC GCGGTGGGGG      300

CCAAAGAAAA AAGGCTATAT GAGGAAAGCA GTGCCCGCCA TTACGACATT TATGCAGGAG      360

AGCACTTTAA GCAGGTTATC AGCATTCAGA CAGAATGGTT TAAAACGCAC TTGTAATTTT      420

AGATAACGAC TTACGGTGGG TTCAACAGAG CCCGCCGTTA TGATAGACGT CAAATGTCGC      480

ATTTTGTAGC TTCGCTTCCG CTGGGCCCTG TAAGGCGCTA CGTTCTCAGG AAGTCTCAGT      540

ATGCTCAGGA ATACTATCCC GATGTCTGTT GGTTACAGGC ACTCGCCGTG AGAAAAGAGT      600

AAGAAATATC CCGGTAACTA ACGGTATAAT AAACAGCATT GATTGAGTTG AAAGTGCATA      660

TCCATATATA TAGCTCTCCA GGCTTACCGC AATCAGAGGA AAAATAAGGA AAACAAGTGA      720

AGCCTGAAAG CACTGGCCTT TTGCTGAAGT GCAAAGTAGC ATAATATTCC AAAAACTCCG      780

GCAAAAGCAC CGAGATACAG GGTGGCCAGT ATTGAGTGCG CTGAGAAGGC TGACACCTGT      840

GGTCTTTCGA AGAGCCATCC TGCCGCAGAA AGTATCAATC CTGCCAGAAA ACACGGTAGC      900

GCGTTAAACG TTATAACAGA GACAGTACAG CTTCTTTTCT TGCATTGGGT GTATATTATG      960

GCATGGATGA TTACGGCTGA AACAAGCGCA AGGATCCCCT GCCAGTGGCT CTCTGTACTT     1020

GTTTTCGTTT CTTCGAGAAG AATACCCGCC AGTGCAACTA TTGCAACAGT TAATCCCGCA     1080

ATCTGCATTG AGTTCGTTTT TTCATTCAAA AATATCACAG AAGCTATCAA AACAGCCACA     1140

GGCATATTCG CAAATATAAT GGAGGCAAGT CCGGAACTGA CATAGGTTTC ACCATAAATC     1200

ATTAATGAAA AAGGAATGGC GAAATAAAAA ATACAGATTC CAAACTGAAA TAATCGTTGT     1260

CCAGGTGGAA ATAAAAGTGG TGTTTTTCTT AACCATGCAA TGCCCATTAA TAATGGTGCC     1320

GCGAACATAA ATCTCATTCC GGTTGCAAAC ACCGGAGGGA TCGTTTCAGC GGCTATCCGC     1380
```

| ATAGCCAGCC ATGTGGTTCC CCAGGTCATT GCAACCAGCA GGAATAATAT CAATATTGTC | 1440 |
| ACTCTGCGCA TAAGACGCTC CCAGTAAAAG GAATTAATTT AACTTTTTAG CTGGAGAAAA | 1500 |
| ATATTTTTTT CTTTACTGTT TTTTCATACT TTTAGAGAAA ATATTTCTCT TTCAGAAGGG | 1560 |
| TGAGATTATG CTGGAAAAAA AAGATAAAGA GCTACTCAGG CTGTTATAGC GCGACTGTAC | 1620 |
| CCTGTGTTTG CAGGATCTGG CTGCGGCTGT CGATTTAACG CCTAATCCCT GCTGGAAGCG | 1680 |
| CATAAAACGG CTTGAAGATG AGGGGATCAT CACTGGTCGG GTCGCCCTGT TGAGCAAGGA | 1740 |
| CAAGCTT | 1747 |

(2) INFORMATION FOR SEQ ID NO: 3:

(i) SEQUENCE CHARACTERISTICS:
        (A) LENGTH: 1988 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Klebsiella pneumoniae
        (B) STRAIN: Clinical Isolate KP-98-22

(ix) FEATURE:
        (A) NAME/KEY: misc_feature
        (B) LOCATION: 1930
        (D) OTHER INFORMATION: /note= "N= adenine or cytosine or
            guanine or thymine"

(xi) SEQUENCE DESCRIPTION: SEQ ID NO: 3:

| AAGCTTAGAA TAAAAAGATT TTTCTTCTTC ATAACTTTCT CCATTTGTA TGTTTATTTG | 60 |
| TTTCGTATCC TTATTATTTT TATTTGGCTT ACATATAAAT AAATACAACA ATAATTAATA | 120 |
| TAGTCAAGAT GTGTATAATA TTATTGACAA ATATATTTTA ATTAGCTAAT TAATAAATGA | 180 |
| ACAGAAAACA AAGGAGAATA AAATGAAATA TTATATGCTA AAACCATTTC GAATAGGAAT | 240 |
| CTTAGAGAAC GATATAACTG TTAAAGAATC AGAACAATAT GTGATTATTG ATATAATTAG | 300 |
| CGGAGAGGAA ATACTTTATT GTGATGATAA TTGTTATTTA ATTACTCCAA CTTTATTGAA | 360 |
| ATCTCTTAAA GATAGCAATC TTACAGGTGT TAATGTTGTA AAGCCTAAAA ATATGAAATT | 420 |
| CAGTATTGAA CACAACATGA ACATCCTAA TAAAAGTTTA AGGGAATGGT ATAGACTAAT | 480 |
| ACCATTTAAG TATGATAGCG GTAAGAATCA GGAAATATTT CTTGATCAAT ACGACAATCT | 540 |
| AATCATAAAT GAACGCATAA AAAATATAAT ATATAATAAG GATGTTCATA GGGTAAAGAG | 600 |
| AGCTTTTATA ACAGAATATG AGATTGATAA AGTAGAGCAT CATGATGAAG AATAATCGA | 660 |
| GCAACCTGTT TTTAAGAAGG AAAATAAAAC CACTTTTAAA GATTGGTGTG TTTTCATGTT | 720 |
| TATTCTTATA ACTATCATTT ATTTGTTTTT TAAATAAGAG GCTGAAAGAT GAATATCAAA | 780 |
| ATCAATGATG GTATTACAGG CGAGATCTTA GTGTTAAATC AAACAACGTT TAACAATGAT | 840 |
| GTGGATACTA TACAGTTAAG AATGACACCA GAGTTTTTAG CCCTTATCAA AAGACATTGT | 900 |
| TCCGGTGCTA TTGATGTGTC TATATCAGCT TTATTAGATT ATGGAATCAA AAAAATATTA | 960 |
| GATGAAAACA TTTCAATCTC AATACAACAA GTTGAGAAAG AAATCGTAAT TGAATCAGTA | 1020 |
| AAGCGTGATA GTAGCATTAT TCCATTTACT ACAGTTAACT ATAGAGCATC AAGAAAAGAC | 1080 |
| ACACGCCCCG TATTCGTGAG ATTGTGTAAA GATCTAAAAT ATAGGTTAAA AGAAATATCT | 1140 |
| CCGACTAAAT ATACACTTTC CGCAATTGGT ATAATAAAGT ATTCGATTGA TACCTTGCTT | 1200 |
| AAAAACAATC AGTGCCTGAT AATAAAAAGT GAGGTTATTT ATGAAAAATA AAACATTGA | 1260 |

```
ATTTATGCTT AATGCTATTC TTTTTGCTAA GTTTCTTTTA TATCAGGATG AGTTCACAAA      1320

TGAAGAGCTT GAACGTGGTG AAGATGTTCG AAACATAAAA GAGCTTTTCG TATTAAAAAA      1380

TAAAGAATGG ATTAATGATA TTAATACAAT AAGATTAAAG GATATTAACC AAGATATTCA      1440

TATATCATCA ACATACATCA TGTCATTAGA TGGAGTGGGT TATTATGCTT TTTCTAATAA      1500

GTCAGAAGAT GAGTTATACC AATATTTAGT TAATGACCTT TGCGATCATT ATATCGCTGT      1560

AAGTGAAATG TCATTGGAAG ACATAGAGGG AGCTTTAGAG GCAATCGAAG AAGATTTGTT      1620

TGATATATAC CGAAGTAATC TATCTTTAGC CAACAAAATG ATTTTAGATG TTTCAAACAG      1680

ATTTAAAATA AAACCTGATT TGAAAAGACC ATTACTCACC ATCGTTTAAA AAGGGCTGTT      1740

AAGCCCCTTT TATATTGTTC ACTGTTTTAT GATGTGCTAT GTTTACCTTC TAACTTAAAT      1800

GTTGAAAAGG ATAAAACATG AGCGCATTAG GGCATTTTAA TAACATTCGC ACTATCAGAA      1860

AAGAAGCCCA TGAGATGGGC TATGCACACCT TCCTTGAGTT CGCTGAAAAG GTTCAAACCG      1920

TTAAGGATGN GTTCCTAAAA GAAGCAGAAG AGGAAAAAGC GAAACAGGCA CTGGTAGAAG      1980

AAAAGCTT                                                              1988

(2) INFORMATION FOR SEQ ID NO: 4:

(i) SEQUENCE CHARACTERISTICS:
        (A) LENGTH: 1484 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
         (A) ORGANISM: Klebsiella pneumoniae
         (B) STRAIN: Clinical Isolate KP-98-33

(xi) SEQUENCE DESCRIPTION: SEQ ID NO: 4:

AAGCTTTTAA TGGAATGAGC GTATTTTTAA ACTAAAAAAA GGATTACATT ATGAATATAT       60

TATCAATAGC ATCAGGCGAA ATAGTGTTTT GTTTATTTAT AGCGTTTTTT ATTTATACAG      120

GCATTAAAAT CAAAAGCAGT AAGAAATTAA CAAAGATATA TAAAAATATA GGATGGGTAG      180

GAGTTGCTTT ATTAGCCTCT TTATTTATAT CAGTTCATTT ATCAAGAGAG GTTCACATTG      240

TTCTATCTCT TATCTTTGTT CACTATTTAA AACTTACTTA TTCAATGACT TTTATTTTGG      300

GTGTTTTCTT CTTAGTAAAG AAAATTTATT CAAAAATAAA AGGTTTTTTC AAGCCAAAGT      360

TTGCGGCATA AGGAGGTTTC AATGAAAGGA CGTAGAAAAG GATTTATCCT GATTGAGTTG      420

TTATTAGTGC TGGTAGTTGC TACTGGCATC GCCGGAGCAA CGTTTTACGG GTATAGCAAG      480

CTGCAGGAAG GGTTCAGAAC AAGCAACGCT ATACGCGATC TGGCTACTAT CAGTAAAGCC      540

ATGAACGCTA TAACAGCTTC TAAGCCCACT ATAGCCGAAG CTAATAGTAT GCTCATCAGT      600

TCAAAGAGTC TTCCTTCTAC GCTGGTAGAC ACCAGAACTA ACACGCTTGT GAATGCCTAT      660

GGCGGTAAGC TCACTATAAC GGCTCACAAC GGCTTGGACG ACTCTTATGA TGTGTCTTTC      720

TACAATGTTC CACTAAGCGC CTGTTCTACG CTTGTAAGCA GCGGTAGGGT GGTTTATAGA      780

AACATAAGCA ACACCACATC AGGATCTAAG ATTGCGGCCA CACCCAGCAT GGCAGACATA      840

ACTGCTTTCT GTTCCAGCTT TAACACCAGT TCAGTGCTTG TTTTTACCAA CGCCGACTAA      900

CCAAAAGCCC CGACCGGGGC TTGTCTTACC TACCTAATAA AAGCCTAATT AACAAATTGA      960

TTTAGCTAGG TTTTATTGGT ACTATCACGC CGATCTGGTG CATAACTGAC CACTTTTATA     1020

ATGAATGAGG GTTGAGTATG AAAAAGTTTA TGGCGGTTGC GGTTATCGGT ATGGCTTCAC     1080
```

```
TTCTGGCAGG TTGTAATGAC GGTATTTATG GCGAATACAT CAGTAAGCAG TATGGGGTAA      1140

GGCTTGATAT TCAAAAGGAC GTAATCAAGT TTAAAGACAG CACCTTTAAT GTTAAGTCAT      1200

GGGATGAAAG CCAAAAACCT GTATACATTG CTAAAACACA AAACAAAGAC ATTGGATCTT      1260

TTACTTTCAA AATTGAGAAA GTAAAACAAG GTGTAGTTTA TCAAGGCGTA GTTTTTGAGA      1320

AGGATTAATC AAATGGAAAA GAAAACTGTT CGCTGTCCTT TTTGTGATCA CGAAACAAAA      1380

CACGGCTTAG GTGTGTGTTT ACCTTGCGGA GCAAACATAA CATACGGTAA AGCACCGTTA      1440

TGGTTTGGTC AAATTGGCGC TTTATTATCT GTCGTATTAA GCTT                      1484
```

(2) INFORMATION FOR SEQ ID NO: 5:

(i) SEQUENCE CHARACTERISTICS:
  (A) LENGTH: 1248 base pairs
  (B) TYPE: nucleic acid
  (C) STRANDEDNESS: double
  (D) TOPOLOGY: linear (ii) MOLECULE TYPE: DNA (genomic)

(vi) ORIGINAL SOURCE:
  (A) ORGANISM: Klebsiella pneumoniae
  (B) STRAIN: Clinical Isolate KP-110-32

(xi) SEQUENCE DESCRIPTION: SEQ ID NO: 5:

```
AAGCTTAAAT GATTTCTTGG ATGATAAAAA ACGCAAAGAA CAGCACAGGA AACGTCTTGC        60

TGATAAGTTG TTTCACACTG TTCGTTCTGG TAGTGATACA GAGATTCAAT CTGTTATAAA       120

AGAATGTTCA GAAAGTGGCT TAGATTTTAA AGATGTAAAA CATGATTACC TGTTAGAATA       180

TTTTGATTCC TTCCATAACC GCTTTACCCC TCCTTCTATT CCCATTATTA AATTACTTAT       240

TAGCTATCAA AATAACATAT CTCATAAAGC CAAGTTAGCA TTTTGCCGCA ATATATATTA       300

TCGTGGGTTT TTAAACGAAG AAGAGTTATA TGAAATATCC GAATTAATTA TAAAATAAAG       360

TCTCAATATA GATTGACTTA TATTTAAAAT CCCTTATAAA TAATAATATA CACAAATAAA       420

TATAAGAGGG TTTTAAATAT GAATGCTATA AAAGAGATTA AAACAATAGC TTTAGCTCAT       480

GGAATATTAA ACGATATAAG AAAAGGTAGG AACCATAACG AAGTTTTCGC AAGTTCAGAA       540

AGAATAGATG TTGATTATTT AACTAACTAT TTAAGTGGTA AACTTGGAAA GAAAATAACA       600

ACTTTCAAAA GACTTGATGG AATCCTTTCT TACAGCAAAA GAAAAGATCA AATAGTATCA       660

GGTTCTGTTT TCTTCTACGC TCCTGAAAAA AATCAGGACA GTGAGAAAGA GGCTCAGTTC       720

CTTAAGTTGT TAACGTTCAA GTTAGCTCAA AACAATTCAT TTTTCATACA TTTTAAAGAC       780

CAAAGAGAAG GAGGATTATA ATGATATTGG ATTCAATCAG TTTTAATGAA CACGATTACC       840

ACTTGGTTTC TAATACAACA GCGACATACG AAATAAAACT AAAAATAGTC AAAGTTTTAC       900

GTGGGCGTAA GTTTGAAAGA TTCAGGGTAG ATAGTCCGTT TGTAGAAATA CTCAAAGTGG       960

CATATGCCCC GGCAGGTAAG AAAAGAGCAA ATGAAACAAC GAGTATTATT GAGCAAATGA      1020

AAGAGGACTT AACAAACATA GTTCTTGAAG AGGCGGTAAA AACACAGGAT AAGGCAATGA      1080

GTTTTATAAA AGGTGATTCA GATGGAGATG ATAAATGATT TATTGGTGTT AGTAAAAACA      1140

AGTGCGTTTG TGATGGGGTT GTATTTTTCA TGTGTTTATA CAGAAAGAAC ACGAAGAAAC      1200

ATTATAAGGG CGTGGTTTAA AAGGAATATA ATAGTTGTTG AAAAGCTT                  1248
```

(2) INFORMATION FOR SEQ ID NO: 6:

(i) SEQUENCE CHARACTERISTICS:
  (A) LENGTH: 24 base pairs

```
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO: 6:

CGACGTTGTA AAACGACGGC CAGT                                               24

(2) INFORMATION FOR SEQ ID NO: 7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO: 7:

CAGGAAACAG CTATGAC                                                       17
```

PROBES FOR THE DIAGNOSIS OF INFECTIONS CAUSED BY *KLEBSIELLA PNEUMONIAE*

FIELD OF THE INVENTION

The present invention relates to a probe which is useful for detecting and identifying *Klebsiella pneunoniae*, the causative bacteria of infectious diseases, specifically, representative bacteria which cause sepsis, as well as *Klebsiella pneumonia*.

BACK GROUND ART

Pathologically, "infection" is defined as an invasion of pathogenic microorganisms (hereinafter referred to as "bacteria") and an establishment of footholds for the growth in the host organism by the pathogenic microorganisms.

Thereafter, the outbreak of the disease states caused by proliferation of the pathogenic microorganisms in vivo depends upon the relationship between the resistance of the host and the toxicity of the bacteria.

The diseases caused by infection of pathogenic microorganisms are called infectious diseases. Generally, bacteremia in the broad meanings is defined as the cases where the phagocytic abilities of the host cells can not overcome the bacterial proliferative abilities, and the bacteria spread over systemically through the blood flow. Among the bacteremia, the disease state wherein the causative bacteria are discharged into the blood flow persistently or intermittently from a particular focus (infection focus) of the host body, thereby new infection focus is built in another part of the body, resulting in the serious systemic symptoms is called sepsis. Particularly, when the body defense mechanisms against the infection are deteriorated due to the underlying disease and the therapeutic treatment for such disease, especially in the disease state of malignant tumor, leukemia, collagen disease or the like, the infection may often lead to sepsis, then even to the shock state, then DIC (disseminated intravascular coagulation), ARDS (adult respiratory distress syndrome) and the like, finally to the death.

Thus, there is a demand for the improvement of the method for rapid diagnosis of the infectious disease because the accurate diagnosis at an early stage of the infection is necessary, which is extremely crucial for the appropriate therapeutic treatment.

Further, when the host suffers from the infectious disease, the phagocytes such as neutrophils, monocytes and macrophages primarily play defensive roles in the tissues in vivo, while the dominantly proliferated bacteria are exited from the phagocytic cells into the host blood flow, then the bacteria will make appearance in the blood.

In the conventional diagnostic procedure, it is mandatory to: (1) analyze the clinical symptoms; (2) culture the specimen for the proliferation of the causative bacteria; (3) identify the causative bacteria isolated from the specimen; and (4) check the shock state of the patient, and then the therapeutic strategy is determined after these items are sufficiently examined. For determinative diagnosis, the causative bacteria must be detected and identified accurately from the specimen such as blood, then the therapeutic treatment should be conducted by administering appropriate antibiotics and the like for killing the identified bacteria. In particular, the possibility of the presence of the drug-resistant strain as well as possible induction of the replacement of bacteria should be considered well, therefore, it is very important to isolate and identify a pathogen, and to select suitable drugs at an early stage based on the drug sensitivity test of the pathogen.

Many of the causative bacteria of sepsis are members of gram-negative rods, and among all of these bacteria, aerobic gram-negative rods such as Pseudomonas, Klebsiella and *Escherichia coli* account for 60 to 70%. Especially, *Klebsiella pneumoniae* is the representative of the causative bacteria of sepsis.

On the other hand, *Klebsiella pneumonia* is a kind of pneumonia which is caused by *Klebsiella pneumoniae*. This pneumonia is characterized by the production of a lot of viscous capsule matter, and the occurrence of the resistant bacteria against the drugs, thus, the prognoses may be unfavorable, often leading to death with complication of septic shock.

Bacteremia including sepsis is a disease state wherein the bacteria exit into the blood, and a large dose of the antibiotics effective for the causative bacteria are administered for the therapeutic treatment thereof. Whereas, since antibiotics generally deteriorate several functions of the organs such as liver, administration of the anti-bacterial agents having no effectiveness to the patient in a critical condition should be avoided at most. Therefore, the rapid and accurate method to identify the causative bacteria has been desired in the clinical field.

As above mentioned, the basis of the therapeutic treatment of the bacteremia including sepsis is to administer proper antibiotics at an earliest stage. In order to accomplish such a rapid treatment, the causative bacteria must be elucidated first. In general, identification of the causative bacteria is conducted by culturing the blood sample from a patient suspected as suffering from bacteremia in the bottle with a culture bottle method, and then culturing the sample as a specimen which showed a positive signal in this method on a selection medium. However, in accordance with such a procedure, at least two separate bottles, containing medium for aerobic bacteria and another for anaerobic bacteria are required. Moreover, a long term culture is necessary and indigenous bacteria on skin may be contaminated in the sample. Additionally, in cases of the diagnosis of the patients who had already been treated with a large dose of antibiotics when the possible bacteremia was suspected, the growth and proliferation of the bacteria may be prevented even if the bacteria are present in the specimen. Accordingly, the feasibility of successful culture of the bacteria from such specimen may become extremely low.

Furthermore, alternative subroutine methods developed heretofore may include: an instrumental analysis method of constituents of bacteria and metabolic products from bacteria (See Yoshimi Benno, "Quick identification of bacteria with gas chromatography", *Rinsho Kensa*, Vol. 29, No.12 pp.1618–1623, November 1985, Igaku Shoin.); a method utilizing a specific antibody (See Japanese Patent Provisional Publication No.60-224068.); and a hybridization method utilizing a specificity of DNA (Japanese Patent Provisional Publication No. 61-502376), however, any of which requires the steps for separation of the bacteria, as well as the steps for culturing and growing the bacteria.

On the other hand, an established method based on the function of the phagocyte in the infectious diseases has been proposed, wherein a stained smear of buffy coat in which leukocytes in the blood sample are concentrated is examined under an optical microscope. Generally speaking, the detection rate of bacteria in buffy coat specimens from adult bacteremia patients is 30% at most, which is similar to that in blood specimens from earlobes, however, it was reported that in case that the patients are newborn children, the bacteria could be detected in seven cases in ten (70%). Therefore, information concerning the presence of bacteria in peripheral blood obtained by a microscopic prospection on a smear can provide an important guiding principle for the therapeutic treatment.

The above mentioned conventional methods necessitate the pretreatment which requires at least three to four days in total, containing one to two days for the selective isolation of bacteria from a specimen, one day for proliferating cultivation, and one or more days for operation of fixation, and the culture thereof should be continued in practice until the bacteria grow enough, therefore, the pretreatment may require one week or more days. In addition, any bacteria other than the causative bacteria may be contaminated during the culture step in some cases, and such contaminants may not be distinguished from the causative bacteria.

More importantly, as mentioned above, because many of the causative bacteria in the specimen to be proliferated and detected have been incorporated into phagocytes, and are already dead or stationary immobilized due to the antibiotics administered, the number of the bacteria that can be grown may be small even under appropriate conditions for the culture of the causative bacteria, thereby, the actual detection rate of bacteria is as low as about 10% when the clinical culture specimen is employed. In the other words, for the present, 90% of the examined blood from the patient clinically suspected as suffering from the infection could not be identified for the presence of the bacteria after all, even though the culture is continued for further one or more days.

Although the determination of the causative bacteria and selection of the antibiotics suitable for killing the bacteria as quick as possible have been eminently desired, in light of the present situation as above, the presently employed practice depends upon a therapeutic treatment which is initiated when the infection is clinically suspected without awaiting the results of the detection of the causative bacteria. That is to say, a trial and error method has been practiced wherein an antibiotic having the effectiveness for the widest range of the causative bacteria is administered first, and next, if the antibiotic is shown to be not effective in one or two days, another antibiotic will be tested.

Moreover, when the method for detecting the bacteria in the specimen by staining them is carried out, skilled experiences are necessary so that the bacteria can be rapidly distinguished, based merely on the shapes seen under a microscope, because the components of the host tissue may also be stained. In such cases, it may be difficult to lead a final determination.

As stated above, although the infectious diseases caused by *Klebsiella pneumoniae* are the diseases of which rapid and accurate diagnosis has been required, the conventional diagnosis method could not have complied with such demands.

DISCLOSURE OF THE INVENTION

The present invention was accomplished in view of the above-described problems in this art, and is directed to probes which have the specific reactivities toward DNA or RNA derived from causative bacteria of infectious diseases, specifically *Klebsiella pneumoniae*, and to elucidation of the nucleotide sequences of the portions of the gene essentially derived from *Klebsiella pneumoniae*, which should be comprised in the probe.

Accordingly, the bacterial DNA still included in the bacteria but in the process of breakdown through ingestion by phagocytes can be significantly detected based on its specificity using hybridization method. Therefore, rapid and accurate detection of the causative bacteria of infectious diseases can be achieved without culturing and proliferation of the bacteria. Moreover, identification of the causative bacteria can be accomplished through DNA amplification using PCR method without the hybridization process when a primer is designed with reference to the nucleotide sequence information of the probes of the present invention.

In addition, the probe used for the hybridization may be labeled with non-radioactive agent. If biotinylated probe is used for example, the detection can be carried out in a general examination laboratory not having a facility for radioisotope handling. Thus, operation for the detection can be practiced in a rapid and simple way.

BRIEF DESCRIPTION OF DRAWINGS

FIG. 1(a) is a drawing which shows the positions of the originated bacterial strains of the DNAs on each of the filters of dot blot hybridization, and FIG. 1(b) shows the results obtained by color development after the hybridization process using each probe.

BEST MODE FOR CARRYING OUT THE INVENTION

In order to explain the present invention in more detail, non-limiting Examples with respect to the probes which are derived from *Klebsiella pneumoniae*, causative bacteria of infectious diseases are shown below.

EXAMPLE 1

DNA Probe Derived from *Klebsiella pneumoniae*

(1) Preparation of DNA Probes Derived from the Bacteria *Klebsiella pneumoniae*

Clinical isolate of *Klebsiella pneumoniae* was cultured overnight in BHI (Brain Heart Infusion) medium, then the cultured cells were harvested, and genomic DNA was extracted therefrom in accordance with Saito-Miura modified method ("Preparation of transforming deoxyribonucleic acid by phenol treatment", *Biochem Biophys. Acta* vol. 72, pp.619–629 (1963)) in which cell lysis step was carried out by adding N-Acetylmuramidase SG to the lysis buffer.

The extracted DNA was completely digested with restriction enzyme HindIII, then random cloned into vector pGEM-3Z. Five probes specific to *Klebsiella pneumoniae*, that is to say, the probes comprising DNA fragments which showed specific reactivities toward DNA included in natural *Klebsiella pneumoniae*, were selected from thus obtained clones.

Thereafter, the selected probes were named: probe KP-77-46, probe KP-85-43, probe KP-98-22, probe KP-98-33, and probe KP-110-32.

(2) Studies of Species Specificity of the DNA Probes Derived from *Klebsiella pneumoniae*

Interactions between each probes and DNAs from several kinds of causative bacterial strains of infections were studied as follows.

First, the clinical isolates and deposited bacterial strains as listed in Table 1 below were prepared. In order to obtain the sources of Human genomic DNA in Table 1 and a control sample, leucocytes which were collected from four healthy adult men, and *Escherichia coli* K-12, JM109 transformant containing plasmid pGEM-3Z were respectively prepared.

TABLE 1

| Bacteria No. | Abbrev. | Name | Origin |
|---|---|---|---|
| 1 | KP | Klebsiella pneumoniae | Clinical Isolate |
| 2 | SA | Staphylococcus aureus | ATCC 25923 |
| 3 | SE | Staphylococcus epidermidis | ATCC 12228 |
| 4 | EC | Escherichia coli | ATCC 25922 |
| 5 | EBC | Enterobacter cloacae | Clinical isolate |
| 6 | EF | Enterococcus faecalis | Clinical isolate |
| 7 | PA | Pseudomonas aeruginosa | ATCC 27583 |
| 8 | BF | Bacteroides fragilis | Clinical Isolate |
| 9 | SP | Streptococcus pyogenes | Clinical Isolate |
| 10 | SAG | Streptococcus agalactiae | Clinical Isolate |
| 11 | SPN | Streptococcus pneumoniae | NYSDH DP-2 |
| 12 | HI | Haemophills influenzae | Clinical Isolate |
| 13 | HPA | Haemophills parainfluenzae | Clinical Isolate |
| 14 | HUM | U937 Human Genomic DNA | |

[ABBREVIATION]
NYSDH: New York State Department of Health (Albany, New York, USA)

Thereafter, the DNAs included in each of the clinical isolates were extracted according to the method described in Example 1(1), then the aliquot of the extracted DNA (e.g., 10–100 ng) was spotted onto a nylon filter. After denaturation with alkali, the filter was subjected to dot blot hybridization. The human genomic DNA sample was prepared from the leukocyte obtained as mentioned previously using Saito-Miura modified method (supra). A control sample was prepared from *Escherichia coli* K-12, JM109 transformant containing plasmid pGEM-3Z using the method for preparation of plasmid DNA described in the following Example 2(1). Hybridization was then carried out overnight using a Digoxigenin-11-dUTP (BRL) labeled DNA probe which was derived from the *Klebsiella pneumoniae* under a hybridization condition of 45% formamide, 5×SSC, at 42° C. according to Manual by Maniatis (T. Maniatis,et al., "Molecular Cloning (A Laboratory Manual Second Edition) "., Cold Spring Harbour Laboratory (1989)).

After overnight hybridization was completed, the samples were washed two times with 0.1×SSC, 0.1% SDS at 55° C. for 20 min. according to the manual, followed by color development and detection using Anti-Dig-ALP conjugates (BRL), thus results of hybridization were revealed. These results are shown in FIG. 1, wherein FIG. 1(a) illustrates the positions of the originated bacterial strains of the DNAs on each of the filters of dot blot hybridization, and FIG. 1(b) illustrates the results obtained by color development after the hybridization process using each of the above mentioned probes KP-77-46, KP-85-43, KP-98-22, KP-98-33, and KP-110-32.

The experimental results with respect to the reactivities between each probes and DNAs from each of the clinical bacteria strains are shown in Table 2 below.

TABLE 2

| Bacteria | | | Probe (Denotation: KP-) | | | | |
|---|---|---|---|---|---|---|---|
| No. | Abbrev. | Name | 77-46 | 85-43 | 98-22 | 98-33 | 110-32 |
| 1 | KP | Klebsiella pneumoniae | + | + | + | + | + |
| 2 | SA | Staphylococcus aureus | – | – | – | – | – |
| 3 | SE | Staphylococcus epidermidis | – | – | – | – | – |
| 4 | EC | Escherichia coli | – | – | – | – | – |
| 5 | EBC | Enterobacter cloacae | – | – | – | – | – |
| 6 | EF | Enterococcus faecalis | – | – | – | – | – |
| 7 | PA | Pseudomonas aeruginosa | – | – | – | – | – |
| 8 | BF | Bacteroides fragilis | – | – | – | – | – |
| 9 | SP | Streptococcus pyogenes | – | – | – | – | – |
| 10 | SAG | Streptococcus agalactiae | – | – | – | – | – |
| 11 | SPN | Streptococcus pneumoniae | – | – | – | – | – |
| 12 | HI | Haemophills influenzae | – | – | – | – | – |
| 13 | HPA | Haemophills parainfluenzae | – | – | – | – | – |
| 14 | HUM | U937 Human Genomic DNA | – | – | – | – | – |

[REMARKS]
+: hybridization signal detected
–: hybridization signal not detected

As is evident from the Tables 1 and 2 above, all of the present probes showed reactivities only to the DNA derived from *Kliebsiella pneumoniae*, while no reactivity (i.e., hybrid formation) was observed toward the DNAs from the every other bacterial species in the genus Klebsiella, as well as the DNAs from the bacterial species other than genus Klebsiella. Thus, the specificity of the probes was demonstrated.

EXAMPLE 2

Analysis of the Base Sequence

Each of the base sequences of the DNA probes (five probes in total) of which species specificity was demonstrated in Example 1 as above was determined according to the following procedure.

(1) Preparation of Plasmid DNA

*Escherichia coli* K-12, JM109 transformant, wherein the sub-cloned insert fragment (to be sequenced) is contained in pGEM-3Z (Promega), was inoculated into 5 ml of Luria-Bactani Medium (bacto-tryptone, 10 g/1L; bacto-yeast extract, 5 g/1L; NaCl, 10 g/1L; adjusted pH to 7.0 with 5N NaOH) and cultured overnight.

The culture liquid mixture was centrifuged (5,000 rpm, 5 min.) to collect the bacteria. One hundred $\mu$l of a solution of 50 mM glucose/50 mM Tris-HCl (pH8.0)/10 mM EDTA containing 2.5mg/ml of lysozyme (Sigma) was added to the precipitate, and left at room temperature for 5 minutes. To the suspension, 0.2M NaOH solution containing 1% of sodium dodecyl sulfate (Sigma) was added and mixed. One hundred and fifty $\mu$l of 5M potassium acetate aqueous solution (pH 4.8) was further added thereto and mixed, then cooled on ice for 15 minutes.

The supernatant collected by centrifugation (15,000 rpm, 15 min.) of the mixture was treated with phenol/CHCl$_3$, and ethanol of two times by volume was added thereto, then the precipitate was again obtained by centrifugation (12,000 rpm, 5min.). This precipitate was dissolved in 100 $\mu$l of a solution of 10 mM Tris-HCI (pH7.5)/0.1 mM EDTA, followed by addition of 10mg/ml RNase A (Sigma) solution, then the mixture was left at room temperature for 15 minutes.

Three hundred μl of 0.1M sodium acetate aqueous solution (pH 4.8) was added to this mixture and treated with phenol/CHCl$_3$, then the precipitate was obtained therefrom by adding ethanol to the supernatant. This precipitate was dried and dissolved in 10 μl of distilled water to give a DNA sample.

(2) Pretreatment for Sequencing

Pretreatment for sequencing was performed with Auto-Read™ Sequencing Kit (Pharmacia).

Concentration of DNA to be employed as a template was adjusted to 5–10 μg in 32 μl of a solution. Thirty two μl of the template DNA solution was transferred to a mini-tube (1.5ml, Eppendolf), and added thereto 8 μl of 2M NaOH aqueous solution, then mixed gently. After instant centrifugation, it was left at room temperature for 10 minutes.

Seven μl of 3M sodium acetate (pH 4.8) and 4 μl of distilled water were added, followed by 120 μl of ethanol, and after mixing, the mixture was left for 15 minutes on ethanol/dry ice. DNA which was precipitated by centrifugation for 15 minutes was collected, and the supernatant was removed carefully. The precipitate thus obtained was washed with 70% ethanol and centrifuged for 10 minutes. Then, after the supernatant was carefully removed again, the precipitate was dried under the reduced pressure.

The precipitate was dissolved in 10 μl of distilled water, then 2 μl of fluorescent primer (0.42 A$_{260}$ unit/ml, 4–6 pmol (Fluorescent Primer; Universal Primer: 5'-Fluorescein-d [CGACGTTGTAAAACGACGGCCAGT (SEQ ID NO: 6)]-3' (1.6 pmol/μl, 0.42 A$_{260}$ unit/ml); Reverse Primer: 5'-Fluorescein-d[CAGGAAACAGCTATGAC (SEQ ID NO: 7)]-3' (2.1 pmol/μl, 0.42 A$_{260}$ unit/ml), and 2 μl of annealing buffer was added thereto, and mixed gently.

After instant centrifugation, the mixture was heat-treated at 65° C. for 5 minutes and rapidly transferred to a circumstance of 37° C. and kept the temperature for 10 minutes. After keeping the temperature, it was left at room temperature for more than 10 minutes, and centrifuged instantly.

Then, the sample was prepared by adding thereto 1 μl of elongation buffer and 3 μl of dimethyl sulfoxide.

Four mini-tubes have been identified with one of the marks of "A", "C", "G" and "T", and, according to the respective mark, 2.5 μl of A Mix (dissolved ddATP with dATP, dCTP, c$^7$dGTP and dTTP), C Mix (dissolved ddCTP with dATP, dCTP, c$^7$dGTP and dTTP), G Mix (dissolved ddGTP with dATP, dCTP, c$^7$dGTP and dTTP), or T Mix (dissolved ddTTP with dATP, dCTP, c$^7$dGTP and dTTP) was poured into each identified tube. Each solution was preserved on ice until use, and was incubated at 37 ° C. for one minute or more before use.

Two μl of diluted T7 DNA polymerase (Pharmacia; 6–8 units/2 μl) was added to the DNA sample, and completely mixed by pipetting or mixing it gently.

Immediately after completion of the mixing, the mixed solution was distributed to 4.5 μl of the four types of the solutions respectively which had been incubated at the same temperature. Fresh tips were used for each distribution.

The solutions were kept for 5 minutes at 37° C., then 5 μl of termination solution was added to each reaction mixture.

Fresh tips were also used for this step. Immediately after incubating the solution for 2–3 minutes at 90 ° C., it was cooled on ice. Four to six u I of the solution per lane was applied for the electrophoresis.

(3) Seguencing on Base Sequences

Sequencing on the base sequences of the probes disclosed in Examples 1 and 2, having the specificity toward DNA from Klebsiella pneumoniae was performed using A.L.F. DNA Sequencer System (Pharmacia) under a condition of the electrophoresis process of 45° C. for 6 hours. Primers were serially designed based on the sequences elucidated from each of the upstream and downstream sequences, and the above described procedures were repeated.

Consequently, all of the entire base sequences of the probe KP-77-46 (SEQ ID NO: 1), probe KP-85-43 (SEQ ID NO: 2), probe 98-22 (SEQ ID NO: 3), probe KP-98-33 (SEQ ID NO: 4), and probe KP-110-32. (SEQ ID NO: 5) were elucidated.

Industrial Applicability

Using the probes according to the present invention, the causative bacteria which were incorporated into the phagocytes can be rapidly and accurately identified directly without proliferation of the bacteria by for example, a hybridization method. In other words, the diagnosis wherein the probes of the present invention are used enables the identification of the causative bacteria with single specimen, further, the necessary time for diagnosis can be diminished to approximately 1 to 2 days, while the conventional method with low detection rate requires 3–4 days, and the resulting detection rate is remarkably improved. Therefore, the present invention provides guiding principles of the therapeutic treatment for the infectious diseases caused by Klebsiella pneumoniae, in addition, the effective treatment in an early stage of the infection can be adopted to the patients, which may lead to a reduction of the mortality.

Additionally, in accordance with the present invention wherein the base sequences of the probes which specifically react with the DNA from Klebsiella pneumoniae among other several causative bacteria of the infectious diseases were elucidated, artificial preparation of these probes has become feasible. Moreover, a part of the information of the base sequences provided herein may be utilized to produce primers, which are useful for rapid diagnosis through amplification of DNA of causative bacteria contained in the clinical specimen by a PCR method.

Furthermore, the rapid identification of the causative bacteria may be carried out by comparing the base sequences of the genomic DNA derived from the clinical specimen with the base sequences provided by the present invention.

As stated above, the present invention provides the desired probe for the diagnosis of the infections, besides, outstanding utilities as guiding principles for the manufacture of the primers for PCR as well as standard sequences which are suitable for the comparison of genomic DNA contained in the clinical specimen can be expected. Moreover, the present invention may exert beneficial effects by providing valuable clues for preparation and development of the novel probes which specifically react with the DNA from the causative bacteria of the infectious diseases.

Further, the base sequence disclosed in the present application was obtained by random-cloning of the genomic DNA derived from the clinical isolates, therefore, the utilities of the base sequences of the present invention should be encompassed to the complementary strand thereof.

Additionally, it may be presumed that DNA obtained from the wild strains might contain the mutated portion. However, as apparent from the disclosure of the Examples above, such mutated DNA portion would not affect the utilities which should be derived from the present invention, comprising the specificity of the probe of the present invention in the hybridization procedure for the diagnosis of the infections, and usages of the information on the base sequences disclosed in the present application for designing the primer to be employed for the PCR techniques with the aim of a rapid diagnosis of the infections.

What is claimed is:

1. A purified nucleic acid useful as a probe for diagnosing infectious diseases, consisting of nucleotied sequence selected from the group consisting of SEQ ID NOS: 1, 2, 3, 4, and 5, and the complement of SEQ ID NOS: 1, 2, 3, 4, and 5.

2. A purified nucleic acid according to claim 1 consisting of the nucleotide sequence set forth in SEQ ID NO: 1, or the complement of SEQ ID NO: 1.

3. A purified nucleic acid according to claim 1 consisting of the nucleotide sequence set forth in SEQ ID NO: 2, or the complement of SEQ ID NO: 2.

4. A purified nucleic acid according to claim 1 consisting of the nucleotide sequence set forth in SEQ ID NO: 3, or the complement of SEQ ID NO: 3.

5. A purified nucleic acid according to claim 1 consisting of the nucleotide sequence set forth in SEQ ID NO: 4, or the complement of SEQ ID NO: 4.

6. A purified nucleic acid according to claim 1 consisting of the nucleotide sequence set forth in SEQ ID NO: 5, or the complement of SEQ ID NO: 5.

7. A purified polynucleotide consisting of a nucleotide sequence selected from the group consisting of SEQ ID NOS: 1, 2, 3, 4, and 5, and the complements of SEQ ID NOS: 1, 2, 3, 4, and 5.

8. A probe for the diagnosis of infectious disease comprising a purified nucleic acid according to claim 1, said nucleic acid further comprising a detectable label.

9. A probe for the diagnosis of infectious disease comprising a purified polynucleotide according to claim 7, said polynucleotide further comprising a detectable label.

* * * * *

UNITED STATES PATENT AND TRADEMARK OFFICE
CERTIFICATE OF CORRECTION

PATENT NO. : 6,225,453 B1  Page 1 of 1
DATED : May 1, 2001
INVENTOR(S) : Ueyama et al.

It is certified that error appears in the above-identified patent and that said Letters Patent is hereby corrected as shown below:

<u>Column 19,</u>
Line 29, "nucleotied" should be -- nucleotide --.

Signed and Sealed this

Eighth Day of January, 2002

Attest:

Attesting Officer

JAMES E. ROGAN
*Director of the United States Patent and Trademark Office*